United States Patent
Haber et al.

(10) Patent No.: US 9,534,001 B2
(45) Date of Patent: Jan. 3, 2017

(54) ORGANOMAGNESIUM SYNTHESIS AGENT

(75) Inventors: Steffen Haber, Frankfurt (DE); Dieter Hauk, Friedberg (DE); Ulrich Wietelmann, Friedrichsdorf (DE); Dirk Dawidowski, Friedberg (DE); Peter Rittmeyer, Sulzbach/Taunus (DE); Jens Roder, Goslar (DE)

(73) Assignee: Chemetall GmbH, Frankfurt am Main (DE)

( * ) Notice: Subject to any disclaimer, the term of this patent is extended or adjusted under 35 U.S.C. 154(b) by 1131 days.

(21) Appl. No.: 12/279,724

(22) PCT Filed: Mar. 5, 2007

(86) PCT No.: PCT/EP2007/052049
§ 371 (c)(1),
(2), (4) Date: Dec. 17, 2008

(87) PCT Pub. No.: WO2007/099173
PCT Pub. Date: Sep. 7, 2007

(65) Prior Publication Data
US 2009/0173914 A1   Jul. 9, 2009

(30) Foreign Application Priority Data
Mar. 3, 2006   (DE) .................. 10 2006 010 410

(51) Int. Cl.
*C07B 49/00*   (2006.01)
*C07F 3/02*   (2006.01)

(52) U.S. Cl.
CPC   *C07F 3/02* (2013.01); *C07B 49/00* (2013.01)

(58) Field of Classification Search
CPC .................................................. C07B 49/00
USPC ......... 252/182.3; 556/453, 480, 96; 514/249
See application file for complete search history.

(56) References Cited

U.S. PATENT DOCUMENTS

| | | | |
|---|---|---|---|
| 2,838,508 A | | 6/1958 | Ramsden |
| 2,872,471 A | * | 2/1959 | Rosenberg et al. ........... 556/480 |
| 3,222,339 A | * | 12/1965 | Fellmann ................ C08F 20/18 526/183 |
| 3,584,027 A | * | 6/1971 | Damle ........................... 556/453 |
| 4,113,758 A | * | 9/1978 | Collins et al. .................. 556/96 |
| 4,169,839 A | | 10/1979 | Houbiers et al. |
| 4,889,940 A | | 12/1989 | Grosvenor et al. |
| 5,371,240 A | | 12/1994 | Slemon |
| 5,512,685 A | | 4/1996 | Jarvinen et al. |
| 6,639,083 B1 | | 10/2003 | Biard et al. |
| 6,676,857 B2 | | 1/2004 | Heeney et al. |
| 7,205,414 B2 | | 4/2007 | Werner et al. |
| 2006/0035898 A1 | * | 2/2006 | Arnold et al. ................ 514/249 |

FOREIGN PATENT DOCUMENTS

| | | |
|---|---|---|
| DE | 198 08 570 C1 | 3/1999 |
| GB | 823958 * | 11/1959 |
| WO | WO 99/43684 | 9/1999 |

OTHER PUBLICATIONS

Tamao, K., et al., "Nickel-Phosphine Complex-Catalyzed Gringnard Coupling-II." Tetrahedron Vo. 38. No. 22, pp. 3347-3354. Feb. 9, 1982.
Aycock, David F., "Solvent Applications of 2-Methyltetrahydrofuran in Organometallic and Biphasic Reactions" Organic Process Research & Development, 1083-6160, 2007.
Poppe, et al. "Convenient Synthesis of Monoprotected 1,2-Diols", Synthetic Communications, 25(24), (1995), pp. 3993-4000.
March, J., Advanced Organic Chemistry: Reactions, Mechanisms, and Structure, 4th Edition, John Wiley & Sons, Inc., 1992, pp. 182-184.
Cotton, F.A., and Wilkinson, G., Advanced Inorganic Chemistry, 5th Edition, John Wiley & Sons, 1988, pp. 159-161.
Great Lakes Chemical Corp., Data Sheet for QO 2-Methyltetrahydrofuran, Nov. 1995, 2 pages.
Kirk-Othmer Encyclopedia of Chemical Technology, 5th Edition, John Wiley & Sons, Inc., 2005, vol. 12, pp. 279-280 and 285.
Kirk-Othmer Encyclopedia of Chemical Technology, 1998, pp. 176-177. 2 pages.
Penn Specialty Chemicals Inc., Data Sheet for Methyltetrahydrofuran, 2005, 8 pages.
Wotiz, J.H. et al., "The Reaction of 1-Alkane with Organometallic Compounds. XII. The Rate of Reaction Ethyl Grignards with 1-Hexane in Certain Ethers", Journal of Organic Chemistry, 1965, vol. 30, pp. 1240-1241.

* cited by examiner

*Primary Examiner* — Monique Peets
(74) *Attorney, Agent, or Firm* — Jeremy J. Kliebert

(57) ABSTRACT

An organomagnesium synthesis agent, a process for preparing this synthesis agent, and its use.

22 Claims, No Drawings

ORGANOMAGNESIUM SYNTHESIS AGENT

This application is a §371 of PCT/EP2007/052049 filed Mar. 5, 2007 which claims priority from DE 10 2006 010 410.2 filed Mar. 3, 2006.

The present invention provides an organomagnesium synthesis agent, a process for the preparation of this synthesis agent and the use thereof.

Within the meaning of the invention, an organomagnesium synthesis agent is a mixture which contains an organomagnesium compound R—MgX and/or R—Mg—R, with R=alkyl, aryl, and X=halide, triflate, tosylate, in an organic solvent. An organomagnesium synthesis agent is used for synthesis, especially for organic synthesis.

In particular, the present invention relates to organomagnesium compounds in a highly concentrated solution.

Organomagnesium compounds are known from the literature. Compounds of this type are synthesised e.g. by reacting mercury organyls with magnesium or by reacting aryl and alkyl halides with metallic magnesium. It is often necessary to use highly activated magnesium for the synthesis, this being obtained e.g. by reduction of magnesium chloride by potassium (Ch. Elschenbroich, A. Salzer, (1993), Organometallchemie, 6.1 Erdalkalimetallorganyle, 3rd edition, $1^{st}$ corrected reprint, Teubner Studienbucher Chemie, Stuttgart).

In preparative organic and organometallic chemistry (review: team of authors, (1990), in Organikum, $18^{th}$ corrected edition, Deutscher Verlag der Wissenschaften, Berlin, pages 495 ff.), organomagnesium compounds are often used for the deprotonation of acidic compounds (R'-A-H, with A e.g. C, O, S, N, P):

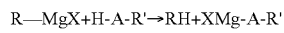

with R=alkyl, aryl, R'=alkyl, aryl, X=halide and A=C, O, S, N, P.

These reagents are also used in halogen-metal exchange reactions, in which an alkyl-, alkenyl, alkynyl- or aryl-bound halogen X' in an organohalide R'X' (with R'=alkyl, aryl) is exchanged with an MgX group (with X=Cl, Br, I, triflate, tosylate or alkyl or aryl). It is also known that an inorganic salt, such as e.g. LiCl, can often be added to these reagents in relatively large quantities (Angew. Chem. Int. Ed. 2003, 42, 4302; Angew. Chem. Int. Ed. 2004, 43, 3333; Angew. Chem. Int. Ed. 2005, 44, 1654; Chem. Commun. 2004, 2288, Organic Letters 2004, 6, 4215; EP-A-1582523) to accelerate the following reactions:

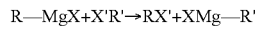

It is also known that organomagnesium compounds of this type are used in C—C cross-coupling reactions. For this purpose, transition-metal catalysts, complexes of Cu, Fe, Ni, Pd and Pt salts, are widely used. In addition to the catalyst, other salts such as e.g. $ZnCl_2$ or $ZnBr_2$ are also often added in up to stoichiometric quantities (L. S. Hegedus, Organische Synthese mit Übergangsmetallen, translated, revised and updated by H.-G. Schmalz and Andre Majdalani, (1995), VCH, Weinheim, pages 81 ff):

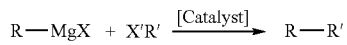

with R=alkyl, aryl, R'=alkyl, aryl, X=halide. Addition reactions of organomagnesium compounds to electrophiles such as nitrites, carbonyls such as carboxylic acid esters, ketones, aldehydes and other groups such as >C=NT, >C=S, —N=O, but also to CC double bonds C=C, are also known.

Organomagnesium compounds are also used in transmetallation reactions with other metal salts $MX_n$ (M=metal, X=halide, n=positive integer). For example, the reaction of $TiX_4$, $ZrX_4$ or $HfX_4$ with suitable organomagnesium compounds leads to the corresponding metal alkyls or aryls $TiR_4$, $ZrR_4$ or $HfR_4$, or in general to compounds of the type $MR_n$, (R=with R=alkyl, aryl, R'=alkyl, aryl, n=positive integer) (U. Zucchini, E. Albizzati, U. Ciannini, J. Organomet. Chem. 1971, 26, 357; P. Shao, R. A. L. Gendron, D. J. Berg, G. W. Bushnell, Organometallics 2000, 19, 509).

Organomagnesium compounds are also used in the synthesis of particular boron compounds. By reacting boric acid esters, such as trimethyl, triethyl or triisopropyl borate, with organomagnesium compounds, alkyl or aryl boranes, alkyl or aryl boronic acid esters or alkyl or aryl borinic acid esters are obtained. The last two groups of substances mentioned form alkyl or aryl boronic acids or alkyl or aryl borinic acids after hydrolysis with water (R. Köster, Annalen der Chemie 1958, 618, 31; review of synthesis and use: D. G. Hall, (2005), Boronic Acids, Wiley-VCH Verlag, Weinheim).

Syntheses of organomagnesium (compounds known to the person skilled in the art and the reaction thereof are also compiled in: K. Nützel, (1973), Organomagnesium-Verbindungen; in Eugen Müller, Houben Weyl, volume 13/2a, fourth edition, Georg Thieme Verlag, Stuttgart; F. R. Busch, D. M. De Antonis, (2000), Grignard Reagents—Industrial Applications and Strategy, in H. G. Richej, Jr, Grignard Reagents New Developments, Wiley, Weinheim; G. S. Silverman, P. E. Rakita, (1996), Handbook of Grignard Reagents, Marcel Dekker, Inc. New York.

It is known to carry out the synthesis of organomagnesium compounds in hydrocarbons, possibly with the addition of amines, or in solvents containing oxygen donors. A preferred oxygen-donor-containing solvent on a laboratory scale is diethyl ether. It is known of diethyl ether that organomagnesium compounds exhibit very high solubility therein and undesirable secondary reactions, such as the coupling of aryl and alkyl halides with the organomagnesium compound (Wurtz coupling), occur only to a small extent (K. Nützel, (1973), Organomagnesium-Verbindungen, in Eugen Müller, Houben Weyl, volume 13/2a, fourth edition, Georg Thieme Verlag, Stuttgart).

A problem with the use of diethyl ether on an industrial scale, however, is its low boiling point (34.6° C.), the associated high vapour pressure (443 mm Hg at 2000), the low flash point (−40° C.), the low ignition temperature (160° C.) and the high explosiveness of vapour/air mixtures (lower explosion limit 1.8%, upper explosion limit 48%). Furthermore, it is known that diethyl ether has a strong tendency to form highly explosive peroxides. On an industrial scale, therefore, the use of diethyl ether is usually avoided (F. R. Busch, D. M. De Antonis, (2000), Grignard Reagents—Industrial Applications and Strategy, in H. G. Richej, Jr, Grignard Reagents New Developments, Wiley, Weinheim, page 167).

For the synthesis of organomagnesium compounds on an industrial scale, other oxygen-donor-containing solvents initially present themselves, such as e.g. tetrahydrofuran (THF), methyl tert-butyl ether (MITBE), diethoxymethane (DEM), dimethoxyethane (DME) or dioxane. However, it is known of these solvents that the formation of the desired organomagnesium compounds from the corresponding aryl and alkyl halides and magnesium is significantly more difficult compared with the synthesis in diethyl ether. In these solvents, accumulations of aryl and alkyl halides can occur during the synthesis, which can react off at an uncontrollable rate. In many cases, owing to the Schlenk equilibrium, a large proportion of undesired diorganomagnesium compounds or even higher coordination polymers is formed in these solvents. It is also known that these solvents tend to form insoluble complexes with magnesium salts. As a result of the high aggregation of the organomagnesium compounds in these solvents in some cases, their reactivity is markedly reduced with respect to addition reactions to electrophiles or Ni, Pd, Pt or Fe complex-catalysed cross-coupling reactions. Secondary reactions, such as the coupling of aryl and alkyl halides with the organomagnesium compound, occur to a large extent in these solvents. The solubility of the organomagnesium compound in these solvents is also generally significantly lower compared with diethyl ether. In some cases, the solubility of the organomagnesium compound can be increased in these solvents by admixing aromatic solvents, such as benzene, toluene, xylenes etc. (K. Nützel, (1973), Organomagnesium-Verbindungen, in Eugen Müller, Houben Weyl, volume 13/2a, fourth edition, Georg Thieme Verlag, Stuttgart).

Also known for the synthesis of particular organomagnesium compounds are particular cyclic ethers, such as tetrahydro-2-methylfuran and tetrahydro-2,5-dimethylfuran. U.S. Pat. No. 2,838,508 discloses the removal of these undesirable ethers from organomagnesium compounds. DE-C-19808570 discloses the special features of the synthesis of benzyl and propen-3-yl magnesium halides in tetrahydro-2-methylfuran. However, in the synthesis of benzyl and propen-3-yl magnesium halides, tetrahydro-2-methylfuran, by shifting the Schlenk equilibrium, leads to the formation of large proportions of dialkylmagnesium compounds such as $(C_6H_5-CH_2)_2Mg$ and $(H_2C=CH-CH_2)_2Mg$. As a result, the unwanted precipitation of relatively large amounts of the corresponding, insoluble magnesium halide occurs during the synthesis. These insoluble magnesium halides have to be separated off at some expense by filtration, with considerable product losses. The precipitation of the magnesium halides has the consequence that the desired Grignard compound is only present in a reduced concentration, and this can, moreover, result in an unwanted change in reactivity.

In order to achieve an optimum and economical space-time yield in reactions of organomagnesium compounds on an industrial scale, it is always of interest to employ the organomagnesium compounds in the highest possible concentration. The substitution options for diethyl ether described are generally able to dissolve a significantly smaller quantity of the organomagnesium compounds at 20° C., and when these solutions are cooled, crystallisation of magnesium halides or organomagnesium compounds generally occurs, so that these solutions usually have to be heated during transport, storage and use, involving a high input of energy. Diethyl ether surrogates which have an increased dissolving power for organomagnesium compounds are not disclosed in the prior art. Furthermore, most of the diethyl ether surrogates mentioned, with the exception of MATBE, have increased miscibility with water. This is significant particularly on completion of the reaction of the organomagnesium compounds and the aqueous work-up of the reaction products and extends the preparation times since the separation takes place only slowly and incompletely. For example, at ambient temperature tetrahydrofuran has unlimited miscibility with water.

The object of the present invention is therefore to provide an organomagnesium synthesis agent which overcomes the disadvantages of the prior art. In particular, this synthesis agent should contain at least one organomagnesium compound in a high concentration. The solvent used in the synthesis agent should exhibit poor miscibility with water and should be safe to use on an industrial scale. In addition, it should be possible to prepare the organomagnesium compound in this solvent, with only very minor or no secondary reactions occurring during the preparation of the organomagnesium compounds.

In particular, the object is surprisingly achieved by an organomagnesium synthesis agent which contains, in addition to at least one organomagnesium compound, a solvent which contains at least one oxygen-donor-containing compound of the general formula 1 or consists of at least one oxygen-donor-containing compound of the general formula 1. These are referred to below as synthesis agents according to the invention and solvents according to the invention.

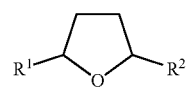

Formula 1 wherein $R^1$ and $R^2$, independently of one another, are selected from: H (where the following applies: if $R^1$=H then $R^2 \neq H$), functionalised or non-functionalised, branched and/or unbranched alkyl, alkyloxy, cycloalkyl and/or cycloalkyloxy groups with 1 to 20 C atoms and/or functionalised and/or nonfunctionalised aryl, hetaryl and/or aryloxy groups with 1 to 12 C atoms.

Examples of $R^1$ and $R^2$ are: H (where the following applies: if $R^1$=H then $R^2 \neq H$) methyl, methoxy, methylmethoxy, ethyl, ethoxy, methylethoxy, n-propyl, propoxy, methylpropoxy, iso-propyl, n-butyl, 2-butyl, iso-butyl, tert-butyl, n-pentyl, iso-pentyl, neo-pentyl, tert-pentyl, hexyl, n-heptyl, iso-heptyl, n-octyl, iso-octyl, 2-ethyl-1-hexyl, 2,2,4-trimethylpentyl, nonyl, decyl, dodecyl, n-dodecyl, cyclopentyl, cyclohexyl, cycloheptyl, methylcyclohexyl, vinyl, 1-propenyl, 2-propenyl, naphthyl, anthranyl, phenanthryl, o-tolyl, p-tolyl, m-tolyl, xylyl, ethylphenyl, mesityl, phenyl, pentafluorophenyl, phenoxy, methoxyphenyl, benzyl, mesistyl, neophyl, thexyl, trimethylsilyl, triisopropylsilyl, tri(tert-butyl)silyl), dimethylthexylsilyl. Preferred is $R^1$=methyl and $R^2$=H (tetrahydro-2-methylfuran).

Surprisingly, it has been found that the solvent according to the invention dissolves organomagnesium compounds other than propen-3-yl and benzyl compounds very well, that this solvent according to the invention are poorly miscible with water and permits safe application. In particular, it has been found in the synthesis of organomagnesium compounds other than propen-3-yl and benzyl compounds that, even in tetrahydro-2-methylfuran as the solvent according to the invention, no shift of the Schlenk equilibrium occurs and therefore no magnesium halides crystallise out of the solution. This is all the more surprising since DE-C-19808570 discloses that this shift of the Schlenk equilibrium occurs.

The solvent according to the invention is distinguished by a high boiling point compared with diethyl ether. The risk of the formation of an explosive atmosphere is therefore reduced on an industrial scale. Thus, for example, tetrahydro-2-methylfuran has a boiling point of 77-79° C.

The synthesis agent according to the invention is prepared by reacting at least one compound of the general formula R—X with magnesium in the solvent according to the invention according to formula 2 or 3, as a result of which the desired organomagnesium compounds are obtained present in the solvent according to the invention:

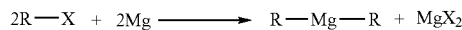

wherein R—MgX and R—Mg—R are organomagnesium compounds, wherein the following apply to R—X, R—MgX and R—Mg—R:

R is selected from: functionalised and/or non-functionalised, branched and/or unbranched $C_1$-$C_{20}$ alkyl groups, $C_1$-$C_{20}$ haloalkyl groups with fluorine and/or chlorine as the halogen atom, $C_1$-$C_{20}$ alkoxy groups, $C_1$-$C_{20}$ haloalkoxy groups with fluorine and/or chlorine as the halogen atom, $C_2$-$C_{20}$ alkenyl groups, $C_2$-$C_{20}$ alkynyl groups, $C_3$-$C_8$ cycloalkyl groups and/or functionalised and/or non-functionalised phenyl, phenoxy, aryl and/or hetaryl groups with 3 to 12 C atoms, which in turn can carry one or more of the aforementioned substituents R; and X is selected from: F and/or Cl and/or Br and/or I and/or triflate and/or tosylate, preferably from Cl and/or Br.

Examples of R are: methyl, trimethylsilylmethyl, ethyl, ethenyl, ethynyl, trimethylsilylethynyl, dimethylthexylsilylethynyl, dimethylcyclohexylsilylethynyl, dimethyltertbutylsilylethynyl, triterbutylsilylethynyl, n-propyl, iso-propyl, cyclopropyl, propyn-3-yl, n-butyl, cyclobutyl, 1-buten-4-yl, 1-butyn-4-yl, 2-buten-4-yl, crotyl, 2 butyn-4-yl, 2-butyl, iso-butyl, tert-butyl, n-pentyl, cyclopentyl, cyclopentadienyl, iso-pentyl, neo-pentyl, tert-pentyl, cyclohexyl, hexyl, n-heptyl, iso-heptyl, n-octyl, iso-octyl, 2-ethyl-1-hexyl, 2,2,4-trimethylpentyl, nonyl, decyl, dodecyl, n-dodecyl, cyclohexyl, cyclohexenyl, cycloheptyl, methylcyclohexyl, vinyl, naphthyl, anthranyl, phenanthryl, o-tolyl, p-tolyl, m-tolyl, xylyl, ethylphenyl, phenyl, 2-fluorophenyl, 3-fluorophenyl, 4-fluorophenyl, pentafluorophenyl, 2-chlorobenzyl, 2-methoxybenzyl, 4-fluorobenzyl, 3-fluorobenzyl, 4-methylbenzyl, 2,5-dimethylbenzyl, naphth-2-ylmethyl, 5,6,7,8-tetrahydronaphth-2-ylmethyl, mesityl, neophyl, thexyl, trimethylsilyl, triisopropylsilyl, tri(tertbutyl)silyl, dimethylthexylsilyl, trimethylsilylethynyl, dimethyltertbutylsilylethynyl, dimethylthexylsilylethynyl, triisopropylsilylethynyl, tritertbutylsilylethynyl, derivatives of substituted and unsubstituted aromatics such as fluorene, indene, indane, sterane, derivatives of substituted and unsubstituted heterocycles such as pyridine, pyrrole, pyrrolidine, pyrazole, imidazole, isoxazole, isothiazole, diazole, triazole, tetrazole, thiophene, furan, dihydrofuran, tetrahydrofuran, pyrimidine, quinoline, isoquinoline, oxane, thiane, piperidine dioxane, dithiane, morpholine, piperazine, pyrane, tetrahydropyrane, dihydropyrane, indole.

According to the invention, the following are preferred as the compound of the formula R—MgX: methylmagnesium chloride, methylmagnesium bromide, ethyl-magnesium chloride, ethylmagnesium bromide, ethynylmagnesium chloride, ethynylmagnesium bromide, vinylmagnesium chloride, vinylmagnesium bromide, n-propylmagnesium chloride, iso-propylmagnesium chloride, cyclopropylmagnesium chloride, n-propylmagnesium bromide, iso-propylmagnesium bromide, cyclo-propylmagnesium bromide, n-butylmagnesium chloride, sec-butylmagnesium chloride, iso-butylmagnesium chloride, tert-butylmagnesium chloride, n-butylmagnesium bromide, sec-butylmagnesium bromide, iso-butylmagnesium bromide, tert-butylmagnesium bromide, phenylmagnesium chloride, phenylmagnesium bromide, 3-fluorophenyl-magnesium chloride, 3-fluorophenylmagnesium bromide, 4-fluorophenylmagnesium chloride, 4-fluorophenylmagnesium bromide.

Excluded from the invention as the compound of the formula R—MgX are benzyl MgX and propen-3-yl MgX and derivatives thereof of the general formula:

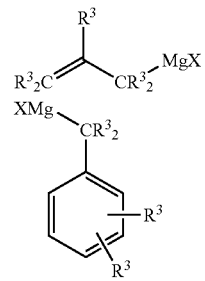

with one or more of the following substituents $R^3$: H, fluorine, chlorine, $C_1$-$C_8$ alkyl groups, $C_1$-$C_8$ haloalkyl groups with fluorine and/or chlorine as the halogen atom, $C_1$-$C_8$ alkoxy groups, $C_1$-$C_8$ haloalkoxy groups with fluorine and/or chlorine as the halogen atom, $C_2$-$C_6$ alkenyl groups, $C_5$-$C_6$ cycloalkyl groups, trimethylsilyl, phenyl and/or phenoxy groups, which in turn can carry one or more of the aforementioned substituents $R^3$; wherein X is selected from: F and/or Cl and/or Br and/or I and/or triflate and/or tosylate.

The solvent according to the invention is distinguished by an excellent dissolving capacity, usually over 20 wt. %, sometimes up to over 30 wt. %, in some cases up to over 50 wt. % of the said organomagnesium compounds.

The synthesis agent according to the invention contains at least one of the organomagnesium compounds according to the invention in a concentration of 20 to 80 wt %, preferably of 30 to 70 wt %, particularly preferably of 35 to 60 wt %.

According to the invention, the synthesis agent according to the invention can be prepared by synthesis of the organomagnesium compounds R—MgX and R—Mg—R, especially compounds of the formula R—MgCl or R—MgBr, in the solvents according to the invention.

The solvent according to the invention can consist of at least one compound of formula 1 or can be present in a mixture with at least one aprotic solvent, in which case the aprotic solvent(s) is/are preferably selected from: benzene, toluene, m-xylene, p-xylene, o-xylene, cyclohexane, methylcyclohexane. The overall proportion of the aprotic solvent or solvents in the synthesis agent according to the invention is 0 to 60 wt. %, preferably from 0.1 to 45 wt. %, particularly preferably from 1 to 30 wt. %, especially preferably from 5 to 20 wt. %.

The synthesis agent according to the invention can additionally contain one or more dissolved inorganic salts, e.g. LiCl, LiBr, $MgCl_2$, $MgBr_2$, $FeCl_3$, CuCl, $CuCl_2$, CuBr, $CuBr_2$, $ZnCl_2$ or $ZnBr_2$, or mixtures of at least two of these salts.

The molar ratio of inorganic metal salt to the organomagnesium compounds according to the invention is 0.1 to 5, preferably 0.3 to 1.5.

According to the invention, the synthesis agent according to the invention can be used in the reaction of organomagnesium compounds with an electrophile or an aryl or alkyl halide or triflate or tosylate or a boric acid ester, especially trimethyl, triethyl or triisopropyl borate.

According to the invention, the synthesis agent according to the invention can be used in a transition-metal-catalysed (Fe, Cu, Ni, Pd or Pt complex with or without the addition of zinc halides such as $ZnCl_2$ or $ZnBr_2$) cross-coupling reaction with an aryl or alkyl halide or triflate or tosylate.

According to the invention, the synthesis agent according to the invention can be used for the reaction of organomagnesium compounds R—MgX or R—Mg—R in transmetallation reactions with other metal salts $MX_n$.

The present invention provides in detail:
an organomagnesium synthesis agent, which contains at least the following components:
a solvent, which contains at least one oxygen-donor-containing compound of the general formula:

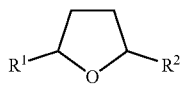

wherein $R^1$ and $R^2$, independently of one another, are selected from: H, functionalised or non-functionalised, branched and/or unbranched alkyl, alkyloxy, cycloalkyl and/or cycloalkyloxy groups with 1 to 20 C atoms and/or functionalised and/or non-functionalised aryl, hetaryl and/or aryloxy groups with 1 to 12 C atoms, wherein the following applies: if $R^1$=H then $R^2 \neq H$;

at least one organomagnesium compound of the general formula R—MgX or R—Mg—R, wherein R is selected from: functionalised and/or non-functionalised, branched and/or unbranched $C_{1-20}$ alkyl groups, $C_1$-$C_{20}$ haloalkyl groups with fluorine and/or chlorine as the halogen atom, $C_1$-$C_{20}$ alkoxy groups, $C_1$-$C_{20}$ haloalkoxy groups with fluorine and/or chlorine as the halogen atom, $C_2$-$C_{20}$ alkenyl groups, $C_2$-$C_{20}$ alkynyl groups, $C_3$-$C_8$ cycloalkyl groups and/or functionalised and/or non-functionalised phenyl, phenoxy, aryl and/or hetaryl groups with 3 to 12 C atoms, which in turn can carry one or more of the aforementioned substituents R, and
X is selected from: F and/or Cl and/or Br and/or I and/or triflate and/or tosylate,
with the proviso that the following compounds are excluded from the compounds of the formula R—MgX: compounds of the formulae benzyl MgX and propen-3-yl MgX as well as derivatives thereof of the general formula:

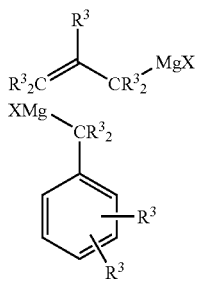

with one or more of the following substituents $R^3$: H, fluorine, chlorine, $C_1$-$C_8$ alkyl groups, $C_1$-$C_8$ haloalkyl groups with fluorine and/or chlorine as the halogen atom, $C_1$-$C_8$ alkoxy groups, $C_1$-$C_8$ haloalkoxy groups with fluorine and/or chlorine as the halogen atom, $C_2$-$C_6$ alkenyl groups, $C_5$-$C_6$ cycloalkyl groups, trimethylsilyl, phenyl and/or phenoxy groups, which in turn can carry one or more of the aforementioned substituents $R^3$;

an organomagnesium synthesis agent, wherein $R^1$ and $R^2$ are selected from: H, methyl, methoxy, methylmethoxy, ethyl, ethoxy, methylethoxy, n-propyl, propoxy, methylpropoxy, iso-propyl, n-butyl, 2-butyl, iso-butyl, tert-butyl, n-pentyl, iso-pentyl, neo-pentyl, tert-pentyl, hexyl, n-heptyl, iso-heptyl, n-octyl, iso-octyl, 2-ethyl-1-hexyl, 2,2,4-trimethylpentyl, nonyl, decyl, dodecyl, n-dodecyl, cyclopentyl, cyclohexyl, cycloheptyl, methylcyclohexyl, vinyl, 1-propenyl, 2-propenyl, naphthyl, anthranyl, phenanthryl, o-tolyl, p-tolyl, m-tolyl, xylyl, ethylphenyl, mesityl, phenyl, pentafluorophenyl, phenoxy, methoxyphenyl, benzyl, mesityl, neophyl, thexyl, trimethylsilyl, triisopropylsilyl, tri(tert-butyl)silyl), dimethylthexylsilyl, wherein the following applies: if $R^1$=H then $R^2 \neq H$;

an organomagnesium synthesis agent, wherein the oxygen-donor-containing compound is tetrahydro-2-methylfuran;

an organomagnesium synthesis agent, wherein the concentration of the organomagnesium compound or compounds is from 20 to 80 wt. %, preferably from 30 to 70 wt. %, particularly preferably from 35 to 60 wt. %;

an organomagnesium synthesis agent, wherein the solvent contains, in addition to the oxygen-donor-containing compound or compounds, at least one aprotic solvent, preferably selected from benzene, toluene, m-xylene, p-xylene, o-xylene, cyclohexane and methylcyclohexane;

an organomagnesium synthesis agent, wherein the overall proportion of the aprotic solvent or solvents in the synthesis agent is 0 to 60 wt. %, preferably from 0.1 to 45 wt. %, particularly preferably from 1 to 30 wt. %, especially preferably from 5 to 20 wt. %;

an organomagnesium synthesis agent which contains an inorganic salt, preferably selected from LiCl, LiBr, $MgCL_2$, Mg $Br_2$, $FeCl_3$, CuCl, $CuCl_2$, CuBr, $CuBr_2$, $ZnCl_2$ or $ZnBr_2$ or mixtures of at least two of these salts;

an organomagnesium synthesis agent, wherein the molar ratio of inorganic metal salt to the organomagnesium compounds according to the invention is 0.1 to 5, preferably 0.3 to 1.5;

a process for the preparation of the organomagnesium synthesis agent according to the invention, which is characterised by the following steps:
initially charging and dispersing magnesium in the solvent according to the invention,
activating the magnesium,
metering a compound of the general formula R—X;

a process for the preparation of the organomagnesium synthesis agent according to the invention, wherein the reaction temperature is kept in the range of −10 to +100° C., preferably in the range of 0 to +40° C.;

the use of the organomagnesium synthesis agent according to the invention in synthesis, preferably in organic synthesis;

the use of the organomagnesium synthesis agent according to the invention, wherein the organomagnesium synthesis agent is reacted with electrophiles, preferably carbonyls, nitrites, carboxylic acid esters, ketones, aldehydes, olefins and/or nitro and/or nitroso compounds, oximes and the sulfur analogues of these compounds, preferably thione compounds;

the use of the organomagnesium synthesis agent according to the invention, wherein the organomagnesium synthesis agent is reacted with acidic compounds in order to deprotonate them;

the use of the organomagnesium synthesis agent according to the invention, wherein the organomagnesium synthesis agent is used in halogen-metal exchange reactions;

the use of the organomagnesium synthesis agent according to the invention, wherein the organomagnesium synthesis agent is used in C—C cross-coupling reactions, preferably with the participation of a catalytically active compound, preferably selected from Fe, Cu, Ni, Pd and Pt complexes, particularly preferably with the addition of zinc halides, preferably selected from $ZnCl_2$ and $ZnBr_2$;

the use of the organomagnesium synthesis agent according to the invention, wherein the organomagnesium synthesis agent is reacted with boric acid esters;

the use of the organomagnesium synthesis agent according to the invention, wherein the organomagnesium synthesis agent is used in transmetallation reactions.

The following examples are intended to explain the invention without its being limited thereto:

EXAMPLE 1

General Synthesis of Organomagnesium Compounds in the Solvents According to the Invention In a gas-tight apparatus containing inert gas, magnesium (Grignard turnings, 1.1 equivalents) is added to the solvent according to the invention and dispersed. The magnesium is activated by a method known from the literature and then the metering of a compound R—X (at least 1 equivalent) is begun. The reaction temperature under standard pressure is in the range of −10 to +100° C., and is preferably kept in the range of 0 to +40° C. The start of the reaction can be recognised by the rise in the reaction temperature. Should no rise in temperature take place, the metering of the compound R—X should be interrupted after no more than about 5% of the metering, and activation of the magnesium should be carried out with the reagents known from the literature (team of authors in Organikum, 18th, corrected edition, Deutscher Verlag der Wissenschaften, Berlin 1990, page 499). After the compound R—X has been metered in full, stirring is continued for one hour and the mixture is filtered through a G3 frit to remove the excess magnesium.

EXAMPLE 2

Preparation and Crystallisation Behaviour of a Solution of 40 wt. % Ethylmagnesium Chloride in tetrahydro-2-methylfuran Magnesium turnings (37.9 g, 1.55 mol) and starter solution (EtMgCl 40 wt. % in tetrahydro-2-methylfuran, 11.43 g) are initially charged into the reactor in 2-MeTHF (175.4 g). When the reaction temperature (25° C.) has been reached, the metering of the ethyl chloride (88.00 g, 1.36 mol) is begun. The ethyl chloride is metered within four hours. The reaction solution is stirred for a further two hours at the reaction temperature after the addition has been completed, before being filtered through a D1 frit.

During cold storage of the solution obtained, no crystallisation is observed down to 0° C.

EXAMPLE 3

Preparation and Crystallisation Behaviour of a Solution of 46 wt. % Ethylmagnesium Bromide in tetrahydro-2-methylfuran The reaction is carried out as in example 1. During cold storage of the solution obtained, no crystallisation is observed down to 10° C.

EXAMPLE 4

Preparation and Crystallisation Behaviour of a Solution of 40 wt % n-propylmagnesium Chloride in tetrahydro-2-methylfuran The reaction is carried out as in example 1. During cold storage of the solution obtained, no crystallisation is observed down to 0° C.

EXAMPLE 5

Preparation and Crystallisation Behaviour of a Solution of 35 wt. % Methylmagnesium Bromide in tetrahydro-2-methylfuran The reaction is carried out as in example 1. During cold storage of the solution obtained, no crystallisation is observed down to −10° C.

EXAMPLE 6

Preparation and Crystallisation Behaviour of a Solution of 39 wt. % Methylmagnesium Bromide in Diethyl Ether (Comparative Example)

The reaction is carried out as in example 1. During cold storage of the solution obtained, no crystallisation is observed down to −15° C.

EXAMPLE 7

Preparation and Crystallisation Behaviour of a Solution of 26 wt. % Methylmagnesium Bromide in Tetrahydrofuran (Comparative Example)

The reaction is carried out as in example 1 During storage of the solution obtained, considerable crystallisation is observed from 15° C.

EXAMPLE 8

Comparative Example Preparation and Crystallisation Behaviour of a Solution of 26 wt. % Ethylmagnesium Chloride in Tetrahydrofuran (Comparative Example)

The reaction is carried out as in example 1. During cold storage of the solution obtained, crystallisation occurs below 10° C.

EXAMPLE 9

Preparation and Crystallisation Behaviour of a Solution of 24 wt. % Propylmagnesium Chloride in Tetrahydrofuran (Comparative Example)

The reaction is carried out as in example 1. During cold storage of the solution obtained, crystallisation occurs below 10° C.

EXAMPLE 10

Preparation and Crystallisation Behaviour of a Solution of 40 wt. % 3,4-difluorophenylmagnesium Bromide in tetrahydro-2-methylfuran (Comparative Example)

The reaction is carried out as in example 1. During cold storage of the solution obtained, crystallisation occurs at −10° C.

TABLE 1

Summary of the examples, crystallisation behaviour of organomagnesium compounds as a function of the solvent

| | | | | Crystallises: (Yes/No) | | |
|---|---|---|---|---|---|---|
| Ex. | Substance | Wt. % | Solvent | 10° C. | 0° C. | −10° C. |
| 2 | EtMgCl | 40 | 2-MeTHF | No | No | Yes |
| 3 | EtMgBr | 46 | 2-MeTHF | No | No | No |
| 4 | nPropMgCl | 40 | 2-MeTHF | No | No | Yes |
| 5 | MeMgBr | 35 | 2-MeTHF | No | No | No |
| 6* | MeMgBr | 39 | Et$_2$O | No | No | No |
| 7* | MeMgBr | 10 | THF | Yes | Yes | Yes |
| 8* | EtMgCl | 20 | THF | Yes | Yes | Yes |
| 9* | nPropMgCl | 20 | THF | Yes | Yes | Yes |
| 10 | 3,4-DifluorophenylMgBr | 40 | 2-MeTHF | No | No | Yes |
| 11** | PhenylMgBr | 45 | 2-MeTHF | No | No | No |
| 12** | PhenylMgBr | 17 | THF | Yes | Yes | Yes |
| 13**# | BenzylMgCl | 22 | 2-MeTHF | Yes | Yes | Yes |
| 14**# | Propen-3-ylMgCl | 15 | 2-MeTHF | Yes | Yes | Yes |
| 15**# | 2-CH$_3$C$_6$H$_4$CH$_2$MgCl | 25 | 2-MeTHF | Yes | Yes | Yes |
| 16**# | 2-ClC$_6$H$_4$CH$_2$MgCl | 24 | 2-MeTHF | Yes | Yes | Yes |

*Comparative example,
**Comparative example from DE-C-19808570,
Crystallisation already occurs during synthesis The examples 2 to 5 and table 1 show that, when the solvents according to the invention are used in examples 2 to 5, synthesis agents according to the invention are obtained which contain organomagnesium compounds in high concentrations, i.e. in concentrations of more than 20 wt. %, without crystals precipitating from the solution when it is cooled down to 0° C., and in some cases down to 10° C. This result is all the more surprising since DE-C19808570 reports that magnesium halide crystals are already formed during the synthesis of propen-3-yl- and benzylmagnesium compounds. The solvents according to the invention thus represent an ideal and safe diethyl ether surrogate for the preparation of organomagnesium compounds other than propen-3-yl- or benzylmagnesium compounds.

The invention claimed is:

1. An organomagnesium synthesis agent, which contains at least the following components:
   i) a solvent, wherein the solvent comprises tetrahydro-2-methylfuran, and
   ii) at least one organomagnesium compound selected from the group consisting of methylmagnesium chloride, methylmagnesium bromide, ethylmagnesium chloride, ethynylmagnesium chloride, ethynylmagnesium bromide, vinylmagnesium chloride, vinylmagnesium bromide, n-propylmagnesium chloride, iso-propylmagnesium chloride, cyclopropylmagnesium chloride, n-propylmagnesium bromide, cyclopropylmagnesium bromide, n-butylmagnesium chloride, sec-butylmagnesium chloride, iso-butylmagnesium chloride, sec-butylmagnesium bromide, iso-butylmagnesium bromide, phenylmagnesium chloride, 3-fluorophenyl-magnesium chloride, 3-fluorophenyl-magnesium bromide, 4-fluorophenylmagnesium chloride, and 4-fluorophenylmagnesium bromide, wherein the organomagnesium compound is in a concentration of about 30 wt % to about 70 wt %, and wherein the organomagnesium synthesis agent does not form crystals when it is cooled down to 0° C.

2. An organomagnesium synthesis agent as in claim 1, wherein the at least one organomagnesium compound is selected from the group consisting of ethylmagnesium chloride, n-propylmagnesium chloride, and methylmagnesium bromide.

3. The organomagnesium synthesis agent according to claim 1, which contains an inorganic salt selected from the group consisting of LiCl, LiBr, MgCl$_2$, MgBr$_2$, FeCl$_3$, CuCl, CuCl$_2$, CuBr, CuBr$_2$, ZnCl$_2$ or ZnBr$_2$ or mixtures of two or more of these salts, and wherein the molar ratio of inorganic salt to the organomagnesium compound is 0.1 to 5.

4. A process for the preparation of an organomagnesium synthesis agent, the process comprising:
   initially charging and dispersing magnesium in a solvent comprising tetrahydro-2-methylfuran;
   activating the magnesium; and
   metering into the solvent at least one compound selected from the group consisting of methyl chloride, methyl bromide, ethyl chloride, ethynyl chloride, ethynyl bromide, vinyl chloride, vinyl bromide, n-propyl chloride, iso-propyl chloride, cyclopropyl chloride, n-propyl bromide, cyclopropyl bromide, n-butyl chloride, sec-butyl chloride, iso-butyl chloride, sec-butyl bromide, iso-butyl bromide, phenyl chloride, 3-fluorophenyl chloride, 3-fluorophenyl bromide, 4-fluorophenyl chloride, and 4-fluorophenyl bromide, wherein the organomagnesium synthesis agent does not form crystals when it is cooled down to 0° C. when the organomagnesium compound is in a concentration of about 30 wt % to about 70 wt %.

5. The process according to claim 4, wherein the reaction temperature is kept in the range of −10 to +100° C.

6. A method comprising conducting an organic synthesis with an organomagnesium synthesis agent according to claim 1.

7. A method comprising deprotonating an acidic compound with an organomagnesium synthesis agent of claim 1.

8. The method according to claim 6, wherein the organic synthesis is a C—C cross-coupling reaction.

9. The method of claim 8, wherein a catalytically active compound is present.

10. The method of claim 8, wherein the catalytically active compound is selected from complexes of Fe, Cu, Ni, Pd and Pt, and wherein the cross-coupling reaction is with an aryl halide, an alkyl halide, alkyl triflate, or alkyl tosylate.

11. The method of claim 10, wherein a zinc halide is present.

12. A method comprising performing transmetallation reactions with an organomagnesium synthesis agent of claim 1.

13. The organomagnesium synthesis agent according to claim 1, which contains an inorganic salt selected from the group consisting of LiCl, LiBr, $MgCl_2$, $MgBr_2$, $FeCl_3$, CuCl, $CuCl_2$, CuBr, $CuBr_2$, $ZnCl_2$ or $ZnBr_2$ or mixtures of two or more of these salts.

14. The organomagnesium synthesis agent according to claim 1 which contains at least one aprotic solvent selected from the group consisting of benzene, toluene, m-xylene, p-xylene, o-xylene, cyclohexane and methylcyclohexane, wherein the proportion of the aprotic solvent or solvents in the synthesis agent is from 1 to 30 wt. %.

15. The organomagnesium synthesis agent according to claim 14 wherein the proportion of the aprotic solvent or solvents in the synthesis agent is from 5 to 20 wt. %.

16. The organomagnesium synthesis agent according to claim 2, wherein the organomagnesium compound comprises 40 wt. % ethylmagnesium chloride, 40 wt. % n-propylmagnesium chloride, or 35 wt. % methylmagnesium bromide.

17. The organomagnesium synthesis agent according to claim 2, wherein the organomagnesium compound is methylmagnesium bromide.

18. The organomagnesium synthesis agent according to claim 17, wherein the organomagnesium compound comprises 35 wt. % methylmagnesium bromide.

19. The process according to claim 4, wherein the at least one compound is selected from the group consisting of ethyl chloride, n-propyl chloride, and methyl bromide.

20. The process according to claim 4, wherein the at least one compound is methyl bromide.

21. An organomagnesium synthesis agent as in claim 1 wherein the organomagnesium synthesis agent does not form crystals when it is cooled down to −10° C.

22. An organomagnesium synthesis agent as in claim 1 wherein the organomagnesium compound is in a concentration of about 35 wt % to about 65 wt %.

* * * * *

UNITED STATES PATENT AND TRADEMARK OFFICE
CERTIFICATE OF CORRECTION

PATENT NO. : 9,534,001 B2  
APPLICATION NO. : 12/279724  
DATED : January 3, 2017  
INVENTOR(S) : Steffen Haber et al.

Page 1 of 1

It is certified that error appears in the above-identified patent and that said Letters Patent is hereby corrected as shown below:

In the Specification

Column 11, Line 53, reads "in some cases down to 10°C" and should read -- in some cases down to −10°C. --.

Signed and Sealed this  
Twenty-first Day of March, 2017

Michelle K. Lee  
*Director of the United States Patent and Trademark Office*